United States Patent [19]

Varma et al.

[11] 4,395,557
[45] Jul. 26, 1983

[54] PHOSPHORUS-CONTAINING IMIDE RESINS

[75] Inventors: Indra K. Varma, New Delhi, India; George M. Fohlen, Millbrae; John A. Parker, Los Altos, both of Calif.

[73] Assignee: The United States of America as represented by the Administrator of the National Aeronautics and Space Administration, Washington, D.C.

[21] Appl. No.: 288,267

[22] Filed: Jul. 30, 1981

Related U.S. Application Data

[63] Continuation-in-part of Ser. No. 175,452, Aug. 5, 1980, Pat. No. 4,276,344.

[51] Int. Cl.$^3$ .................. C07D 207/26; C07D 209/34
[52] U.S. Cl. ..................................... 548/413; 548/415
[58] Field of Search ....................... 260/326 E, 326.26; 548/413, 415

[56] References Cited

U.S. PATENT DOCUMENTS

| | | | |
|---|---|---|---|
| 4,166,168 | 8/1979 | D'Alelio | 260/326.26 X |
| 4,168,360 | 9/1979 | D'Alelio | 260/326.26 X |
| 4,168,366 | 9/1979 | D'Alelio | 260/326.26 X |
| 4,168,367 | 9/1979 | D'Alelio | 260/326.26 X |
| 4,276,344 | 6/1981 | Frosch | 428/902 X |
| 4,316,843 | 2/1982 | Waitkus et al. | 260/326 E X |
| 4,316,844 | 2/1982 | Waitkus et al. | 260/326 E X |
| 4,316,845 | 2/1982 | D'Alelio et al. | 260/326 E X |
| 4,321,198 | 3/1982 | D'Alelio et al. | 260/326 E X |

*Primary Examiner*—Joseph Paul Brust
*Attorney, Agent, or Firm*—Darrell G. Brekke; John R. Manning

[57] ABSTRACT

Bis- and tris-imides derived from tris(m-aminophenyl) phosphine oxides by reaction with maleic anhydride or its derivatives, and addition polymers of such imides, including a variant in which a mono-imide is condensed with a dianhydride and the product is treated with a further quantity of maleic anhydride. Such monomers or their oligomers may be used to impregnate fibers and fabrics which when cured, are flame resistant. Also an improved method of producing tris(m-aminophenyl) phosphine oxides from the nitro analogues by reduction with hydrazine hydrate using palladized charcoal or Raney nickel as the catalyst.

8 Claims, No Drawings

PHOSPHORUS-CONTAINING IMIDE RESINS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

DESCRIPTION

This application is a continuation-in-part of our copending application Ser. No. 175,452, filed Aug. 5, 1980, now U.S. Pat. No. 4,276,344 issued June 30, 1981.

TECHNICAL FIELD

This invention relates to addition polyimide resins and to fiber or fabric-reinforced composites made from them.

BACKGROUND ART

Strong light-weight composites can be made by embedding various types of fibers or fabrics in a resin matrix. The polymer used for such a matrix is generally an epoxy resin, although several other resins such as phenolic, novolac, poly(ether-sulfone), poly(phenyl-sulfone), and bismaleimide resins have also been used for certain applications. As fibers or fabrics, carbon and graphite products have been quite useful in the composite structures.

The search for flame resistant materials to form laminates that can be used with greater safety in places such as aircraft cabins, has led to the selection of high temperature resins such as bismaleimides which have high anaerobic char yield (Scientific & Technological Aerospace Reprints, 1976, 14-16, Abstract N76-25354), and to the inclusion of phosphorus-containing compounds either in a mixture with or as an integral part of the resin used as matrix. Searle, in U.S. Pat. No. 2,444,536, discloses a widely used method for the preparation of maleimide polymers. As to the use of phosphorus-containing compounds, Kourtides et al. (Proceedings of the Adhesive for Industry Conference, El Segundo, CA, June 24-25, 1980) have shown substantial improvement in various properties of certain epoxy resins by preparing them with a bis(3-aminophenyl)methylphosphine oxide or its bisphenol analog, instead of the conventional diamine or phenol monomers or curing agents of the art. In summary, however, it can be stated that while the introduction of phosphorus into organic polymers has generally resulted in reduced flammability, increased adhesion, and better solubility in polar solvents, none of the resins used in the composite art are non-flammable.

In copending application Ser. No. 175,452, filed Aug. 5, 1980, entitled "Phosphorus-Containing Bisimide Resins" now U.S. Pat. No. 4,276,344 issued June 30, 1981, bisimides are prepared from phosphine oxides by a reaction typified by the following:

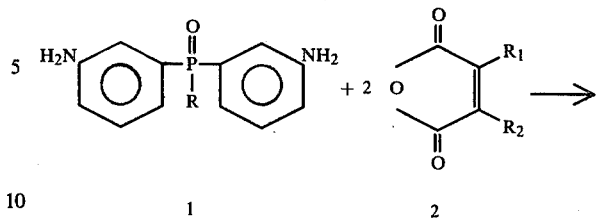

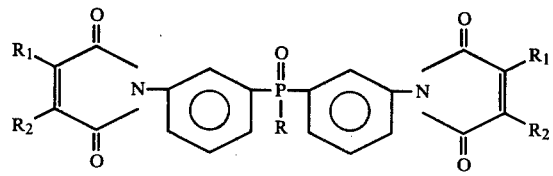

($R_1$ and $R_2$ = H, $CH_3$, Cl)

The monomers(bisimides) 3 can be used to impregnate fibers and cloth and, upon polymerization, confer fire resistant qualities on the fiber or fabric.

It is an object of the present invention to provide improvements upon such monomers, polymers and impregnated fibers and fabrics.

DISCLOSURE OF THE INVENTION

We have found that the trisamino precursor typified by the following:

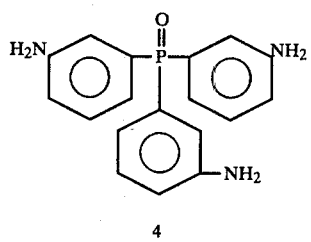

can be used in place of the bisamino precursor. This results in curing at a lower temperature, e.g., 180° C., with good fire resistance. A further advantage is the greater ease of preparing the trisamino precursors.

We have also found an improved method of reducing the nitro precursors of these trisamino compounds, wherein the nitro groups are reduced using hydrazine hydrate as the reducing agent and palladium/charcoal or Raney nickel as a catalyst.

DETAILED DESCRIPTION OF THE INVENTION

Using the triamine 4 and the anhydride 2 as models, and in a variant using also a coupling agent (a dianhydride), the following monomers result.

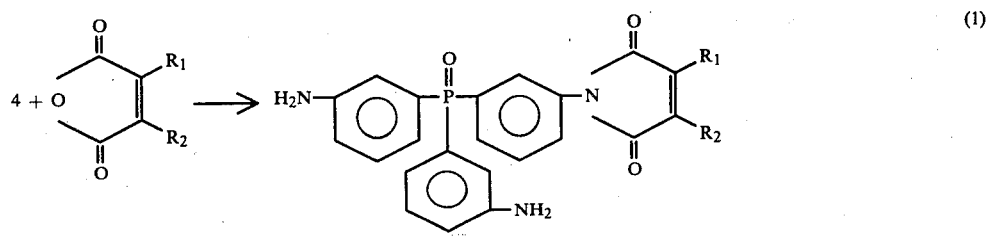
(1)
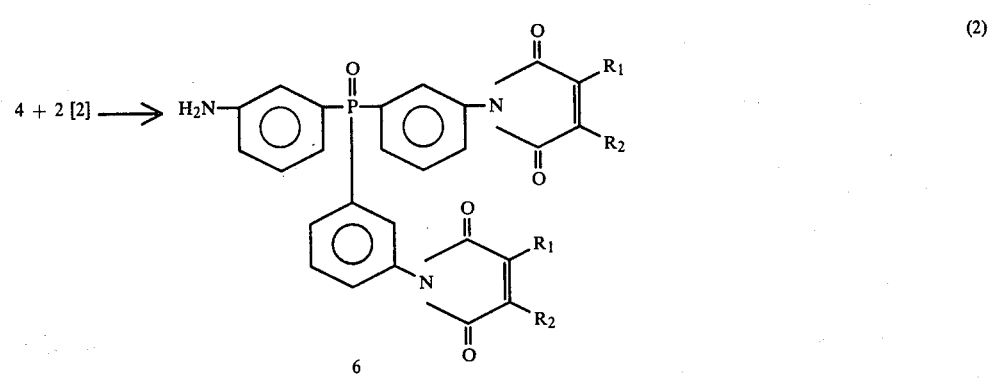
(2)
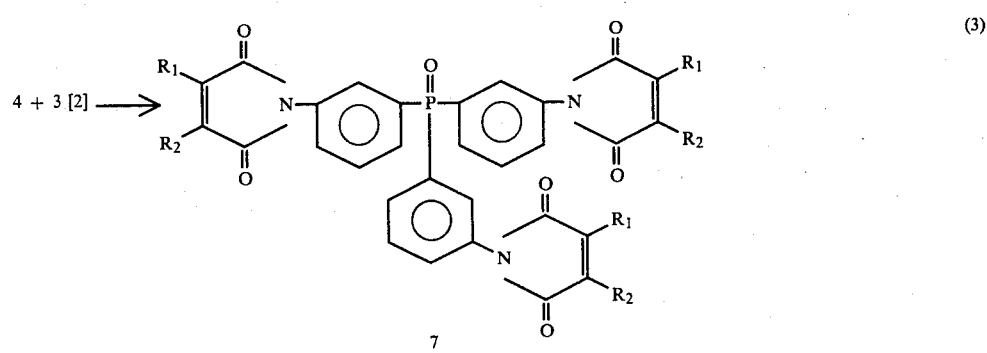
(3)
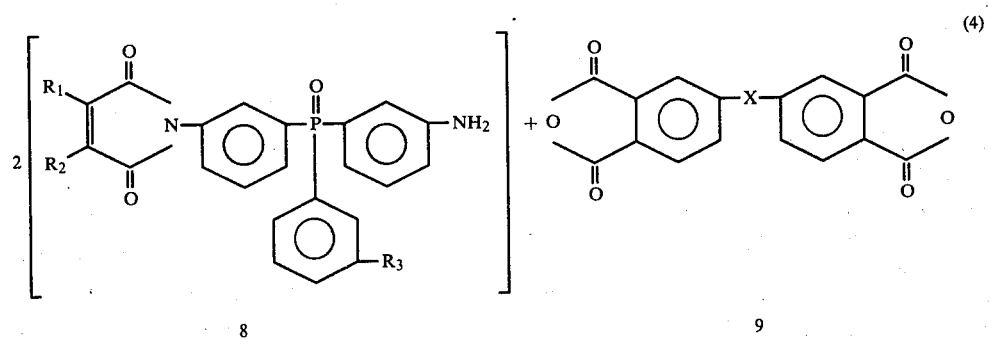
(4)
In the equations above, $R_1$ and $R_2$ may be H, lower alkyl (e.g., methyl, ethyl, etc.), chlorine, or such other atoms or groups as are compatible with the respective reactions and with polymerization of the monomers.

X is a linking entity which may be a valence bond, a bivalent atom (e.g., >O or >S or a bivalent group, [e.g.,—$C_nH_{2n}$—(n=1, 2, 3, etc.)], >C=O, >C=S, >C(CF_3)_2, >SO_2 or any other bivalent group which is compatible with reaction (4) and with polymerization of the monomers. $R_3$ is —$NH_2$ or the imide group.

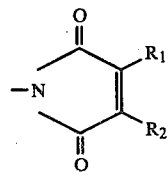

Further, the benzene rings may be substituted by functional and/or non-functional groups provided they do not interfere with the reactions involved in forming the monomers and provided they do not interfere with polymerization and with thermal stability of the polymers. Examples of substituents are alkyl, e.g., $C_1$ to $C_5$ straight and branched chain alkyl; chlorine; aryl, e.g., phenyl and tolyl. Condensed ring phosphine oxides may be used.

Polymerization is accomplished thermally or by means of a catalyst such as cobalt or other metal naphthenates together with peroxides. Partial polymerization may be carried out with the monomer; fibers or fabric may then be impregnated with the resulting oligomer or lower polymer; and the impreganted material may then be cured at a higher temperature. The trisimides polymerize by opening of the olefinic double bonds. With the bisimides nucleophilic addition of the free amino group to the double bond may also occur.

The linking groups illustrated in 10 above result in polymers having diminished cross linking density, hence in impregnated fabrics having greater toughness.

The phosphine oxide component of the imides of this invention can be made from triphenylphosphine oxide by nitration, followed by reduction of the nitro group to the amino group by, for example, stannous chloride dihydrate and concentrated hydrochloric acid, or by hydrazine hydrate and palladized charcoal.

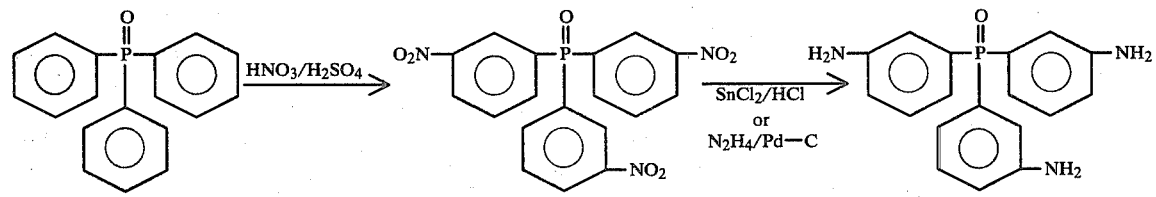

Imides can be prepared by reacting stoichiometric quantities of the reactants in a polar solvent (e.g., dimethyl formamide, dimethylacetamide, N-methyl pyrrolidone, etc.) and cyclodehydrating the intermediate amic acid by sodium acetate and acetic anhydride. Alternatively refluxing the reactants in glacial acetic acid or dimethyl formamide can also be used to prepare imides. The resulting imides can be cured in the temperature range of 180°–300° C.

The resins produced according to the process just described are suitable for many applications in which good adhesion and excellent resistance to heat, fire, solvents and chemicals are required. In the aerospace industry, the new resins may be used as adhesives and as matrix material for fiber-reinforced lightweight composites. To produce such composites, the imide resins are dissolved in solvents such as dimethyl formamide and glass fibers or carbon fibers or synthetic organic fibers in the form of filaments or fabric are impregnated with the solution. The solvent is then removed by evaporation in an air oven at 125°–135° C. and layers of the impregnated fiber materials are formed by means of pressure and high temperature into the desired molded laminate. The laminate is then cured at, for example, 180°–200° C.

The imide resins according to the present invention have noteworthy advantages over the imide resins of the aforesaid copending application. The curing of these resins can be done at relatively low temperatures while retaining the outstanding flame resistant properties of the laminates. Furthermore, the tris(aminophenyl)phosphine oxide is more easily obtained than the bis(aminophenyl)methylphosphine oxide.

The following examples serve to illustrate the present invention.

EXAMPLE 1

Tris(m-aminophenyl)phosphine oxide, 24.25 g, was placed in a flask with 110 ml dimethyl formamide (DMF). Maleic anhydride was added (7.35 g) in two portions over a period of ten minutes. The solution was stirred at 50° C. for one hour. Benzophenone tetracarboxylic dianhydride (BTDA) (12.15 g) was then introduced and stirring was continued overnight. The solution was then heated at 145° C.±2° C. for one hour and then refluxed for 30 minutes. The polymerization product obtained in this manner can further be processed as follows:

The graphite fabric (8 harness satin-weave designated as style 133 fabric) is coated with this resin solution. The impregnated fabric is then dried in a circulating air oven at 125°–135° C. for 20 minutes. Several pre-impregnated graphite fabric pieces are placed one upon the other (4–9 plies) into a platen press and the laminate is hardened under a pressure of 125 psi and a temperature of 180° C. for 150 minutes. Post-curing of the hardened laminate was done at 220° C. for 16 hours. Physical properties of such laminates were tested by an Instron Tensile Tester. A laminate having 21–22% resin was found to have a short beam shear strength of 3300 psi and a flexural strength of 96,040 psi. The laminate did not burn in pure oxygen. The glass transition temperature of a 4-ply laminate was found to be 385° C. No delamination was observed by boiling these laminates in water for 20 hours.

Alternatively, the imide monomer can be isolated from the DMF solution by precipitating it with water and washing with boiling methanol and acetone. Curing of this resin was done thermally at 180° C., 225° C., and 232° C. and an anaerobic char yield of cured resin was found to be 68–70%. Elemental analysis gave following results: C=65.16%, H=3.54%, N=7.12%, P=4.40%.

The values calculated for formula $C_{61}H_{38}P_2O_{11}N_6$ are $C=67.03$, $H=3.47\%$, $N=7.69$, $P=5.67\%$.

EXAMPLE 2

Tris(m-aminophenyl)phosphine oxide 4.27 g, was dissolved in 25 ml DMF and 2.69 g of maleic anhydride added. The solution was stirred at 50° C. for one hour. BTDA (2.09 g) was then introduced and solution stirred overnight. The solution was heated at 145° C.±2° C. for 45 minutes and refluxed for 10 minutes.

A graphite cloth laminate was cured in a manner similar to that described in Example 1. This material had a glass transition temperature of 314° C. as obtained by DMA.

Trisimide monomer could be isolated by precipitation from the DMF solution with water. An anaerobic char yield of 62–69% was obtained. Elemental analysis showed the following results: $C=64.40\%$, $H=3.6\%$, $N=6.92\%$, $P=5.41\%$. The values calculated for formula $C_{69}H_{38}P_2O_{15}N_6$ are $C=66.13\%$, $H=3.03\%$, $N=6.71$, $P=4.95\%$.

EXAMPLE 3

Tris(aminophenylphosphine oxide) 1.615 g and dichloromaleic anhydride 2.49 g were dissolved separately in glacial acetic acid and mixed. This solution was then refluxed gently for 2½ hours. The trisimide was isolated by precipitation in water. The yellow precipitate was dissolved in and recrystallized from chloroform and petroleum ether. The anaerobic char yield of the polymer formed from this monomer by curing at 305° C. for 30 minutes was found to be 65%.

EXAMPLE 4

Tris(aminophenyl)phosphine oxide 1.61 g and citraconic anhydride 1.12 g were separately dissolved in glacial acetic acid. The two solutions were mixed and gently refluxed for 2½ hours. The imide was isolated by precipitation in water. The precipitates were dissolved in acetone and solution was concentrated. The imide was recovered by addition of petroleum ether. Elemental analysis gave following results: $C=65.33\%$, $H=4.45\%$, $N=7.31\%$ and $P=5.42\%$. Calculated values for the formula $C_{28}H_{22}PO_5N_3$ $C=65.75\%$, $H=4.30\%$, $N=8.21\%$ and $P=6.06\%$. Anaerobic char yield of resin cured at 232° C. for 2 hours was 62.5%.

EXAMPLE 5

Tris(aminophenyl)phosphine oxide 1.61 g was dissolved in 10 ml DMF and 1.62 g of maleic anhydride added. The solution was stirred overnight and then heated at 135°–145° C. for 50 minutes and refluxed for another 10 minutes. The trismaleimide was isolated by precipitation in water and recrystallized from acetone and petroleum ether. The anaerobic char yield of the imide resin formed by curing at 232° C. for 2 hours was found to be 64.5%.

EXAMPLE 6

Alternatively, the trismaleimide was prepared by dissolving 1.62 g of maleic anhydride and 1.61 g of the triamine 4 separately in 25 ml of glacial acetic acid. The solutions were then mixed and refluxed for 12–15 hours. Imide monomer was isolated by precipitation in water and filtration. The residue was washed several times with sodium bicarbonate solution until free from acid. After drying, the purification was done with chloroform and petroleum ether.

Trismaleimide was also prepared by dissolving 1.61 g of triamine 4 in 10 ml dimethylformamide and adding 1.62 g of maleic anhydride. The solution was stirred at room temperature for 1 hour and then 0.5 g of fused sodium acetate was added followed by 3.5 ml of acetic anhydride. The solution was stirred at 60° C. for 2 hours. Trismaleimide was isolated as mentioned above.

EXAMPLE 7

Triscitraconimide was also prepared by carrying out cyclodehydration with fused sodium acetate and acetic anhydride as in Example 6. Alternatively the condensation reaction of triamine and citraconic anhydride was done in glacial acetic acid by reacting 1.61 g of amine with 1.85 g of citraconic anhydride and refluxing the solution for 12–15 hours. Triscitraconimide was isolated by precipitation in water and filtration. Further process was similar to Example 6.

As stated above, we have also discovered an improved method of reducing tris(nitrophenyl)phosphine oxides to the triamino compounds. This improved method employs hydrazine hydrate as the reducing agent and a palladium/charcoal or Raney nickel catalyst. These systems have been used heretofore to reduce nitro groups in mono- and dinitroaromatic compounds; see Furst, Chem. Rev. 65, 51 (1965) and Fieser and Fieser, "Reagents for Organic Syntheses", p. 440 (1967), John Wiley. However, as far as we know, such systems have not been employed to reduce nitrophenylphosphine oxides. The system may be used to reduce nitro groups in dinitro compounds such as 1 above or trinitro compounds such as 4 above. The following examples will illustrate this aspect of our invention.

EXAMPLE 8

41.3 g of the trinitro oxide 11 (0.1 mol) (m.p. 244°–245° C.) and 420 ml of 95% ethanol were placed in a 1 l three-necked flask equipped with a reflux condenser, thermometer and dropping funnel. 1.70 g of 10% palladium on carbon (ROC/RIC) was added and the mixture warmed to 35°–40° C. Stirring was done with a magnetic stirrer. About 38 ml of hydrazine hydrate (0.75 mole) (Baker Chem. Co., 99%) was added from the dropping funnel over a 40 minute period. The reaction is exothermic and addition of hydrazine has to be done dropwise. 0.3 g more of Pd/C was then added and mixture refluxed for 1 h. The hot solution was then filtered with gentle suction through a thin layer of Celite. The flask was rinsed with hot ethanol and the catalyst and Celite were washed with it. The combined filtrates on cooling gave white crystals of triamine which were collected by filtration and suction dried. The precipitates after washing with water were dried in a vacuum oven at 80° C., yield=28–29 g (88–89%, m.p. 258°–263° C.). The filtrate was concentrated under reduced pressure and when the volume was reduced to about 30 ml it was added to water. A second crop of white precipitate of amine was obtained (1–1.5 g).

For easier control the hydrazine hydrate can be diluted with alcohol before addition. The Pd/C can be reused.

Elemental analysis of the amine gave following results: $C=66.7\%$, $H=5.67\%$, $N=12.95\%$, $P=9.98\%$ Calculated values for $C_{18}H_{18}N_3PO$: $C=66.81\%$, $H=5.61$, $N=13.0\%$, and $P=9.6\%$

EXAMPLE 9

Bis-(m-aminophenyl)methyl phosphine oxide was also prepared in a similar way by reduction of the dinitro compound. The alcoholic filtrate was concentrated under reduced pressure to a small volume and then amine was precipitated by adding an equal volume of toluene: petroleum ether. (yield=80%, m.p. 145°–149° C.).

In the mass spectra of these amines M-1 ion was the base peak. Eight most intense peaks, i.e., fragment ion values are listed in order to decreasing relative abundances (base peak is given first). Tris(m-aminophenyl)-phosphine oxide: 322, 323, 93, 65, 229, 182, 230.

Bis(m-aminophenyl)methylphosphine oxide: 245, 246, 65, 92, 93, 231, 214, 63. The infra-red spectra of the amines showed characteristic absorption due to amino and P=O groups.

The trinitro compound 11 of Example 8 and the dinitro compound of Example 9 were, respectively, the m-nitro compounds.

We claim:

1. Imides having the structure

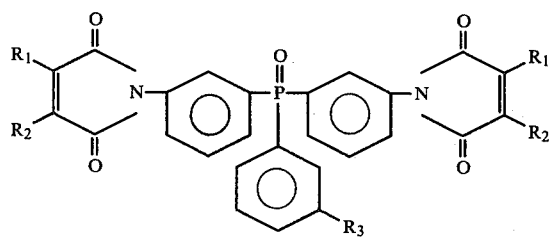

wherein $R_1$ and $R_2$ are selected from the class consisting of chloro, lower alkyls and hydrogen and $R_3$ is the amino group or an imide group

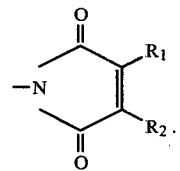

2. Imides of claim 1 wherein $R_3$ is the amino group.
3. Imides of claim 1 wherein $R_3$ is an imide group.
4. Imides of claim 1 wherein $R_1$ and $R_2$ are each hydrogen.
5. Monomers having the structure

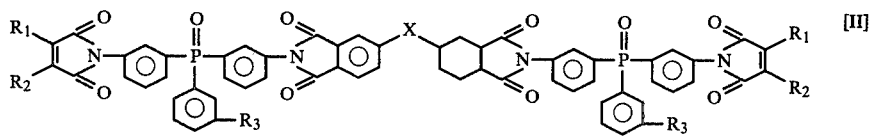

wherein $R_1$ and $R_2$ are selected from the class consisting of hydrogen chloro, and lower alkyls, $R_3$ is —NH$_2$ or the imide group

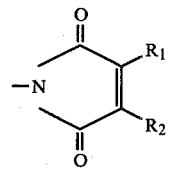

and wherein X is a linking entity selected from the class consisting of a valence bond, —O—, —S—, —C$_n$H$_{2n}$— wherein n is 1, 2 or 3, $$-\underset{\underset{O}{\|}}{C}-, -\underset{\underset{S}{\|}}{C}-, -\underset{\underset{CF_3}{|}}{\overset{\overset{CF_3}{|}}{C}}-$$

and —SO$_2$—.

6. Monomers of claim 5 wherein $R_3$ is an amino group.
7. Monomers of claim 5 wherein $R_3$ is an imide group.
8. Monomers of claim 5 wherein $R_1$ and $R_2$ are each hydrogen and X is

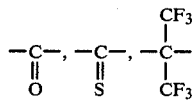

* * * * *